(12) United States Patent
Nakaie et al.

(10) Patent No.: US 6,797,829 B1
(45) Date of Patent: Sep. 28, 2004

(54) SYNTHESIS OF A NOVEL PARAMAGNETIC AMINO DERIVATIVE (EPM-5) FOR LABELLING CHEMICAL AND BIOLOGICAL MACROMOLECULES

(75) Inventors: Clóvis Ryuichi Nakaie, São Paulo (BR); Mineko Tominaga, São Paulo (BR); Antonio Cechlli Matto Paiva, São Paulo (BR); Simone dos Reis Barbosa, São Paulo (BR); Reinaldo Machetto, São Paulo (BR); Shirley Schreier, São Paulo (BR)

(73) Assignee: Conselho Nacional de Desenvolvimento Cientifico e Tecnologico CNPQ (BR)

( * ) Notice: Subject to any disclaimer, the term of this patent is extended or adjusted under 35 U.S.C. 154(b) by 218 days.

(21) Appl. No.: 10/018,842
(22) PCT Filed: Jun. 21, 2000
(86) PCT No.: PCT/BR00/00068
§ 371 (c)(1), (2), (4) Date: Dec. 21, 2001
(87) PCT Pub. No.: WO00/78715
PCT Pub. Date: Dec. 28, 2000

(30) Foreign Application Priority Data
Jun. 22, 1999 (BR) .............................. 9903137

(51) Int. Cl.$^7$ ..................... C07D 207/46; C07D 295/24
(52) U.S. Cl. ........................ 548/528; 548/531; 530/300
(58) Field of Search ................................ 548/528, 531; 530/300

(56) References Cited

U.S. PATENT DOCUMENTS 3,966,764 A  6/1976  Goldstein et al.

*Primary Examiner*—Joseph K. McKane
*Assistant Examiner*—Kamal Saeed
(74) *Attorney, Agent, or Firm*—Morrison & Foerster LLP

(57) ABSTRACT

The present invention refers to the synthesis and application of 2,2,5,5-tetramethylpyrrolidine-N-oxyl-(9-fluorenylmethyloxycarbonyl)-3-amine-4-carboxylic acid, a novel paramagnetic amino acid derivative (spin label), denominated Fmoc-Poac. Fmoc-Poac can be coupled to peptide sequences and other molecules or systems. It can be inserted anywhere in a peptide segment, even at an internal position if necessary, after removal of its temporary amine protecting group, Fmoc. Owing to its pyrrolidine structure, this molecule may induce differentiated conformations as compared with normal α-amino acids, thus being a valuable probe for structural-biological activity of several relevant peptides. The Poac-angiotensin II analogue was synthesized as a model according to its use as a chemical derivative.

7 Claims, 8 Drawing Sheets

Structure of Fmoc-Poac.

Mass spectrum of POAC.

HPLC profile of 2,2,5,5-tetramethyilpyrrolidine-1-oxil-3-amine-4-carboxylic acid (Poac). Experimental conditions: $C_8$ (4,6 x 150 mm) column. Eluent A: $NaH_2PO_4$ 0,1M/water and, B: acetonitrile 90%/water ; 1-21% of B in 10 min.

RPE spectra of 1 x 10$^{-4}$ M (A) Poac in water, pH 5; (B) Fmoc-Poac in dimethylformamide.

Figure 5: Mass spectrum of Fmoc-POAC.

HPLC profile of Poac[7] - AII. Column RF $C_{18}$ (4,6 x 150 mm). Eluent A: 0,1% aqueous TFA and eluent B, 0,1% TFA in 60% aqueous acetonitrile. Flow rate, 1.5mL/min. Elution was performed by a linear gradient of 5% to 95% eluent B.

Mass spectrum of Poac[7]-Angiotensin II.

RPE spectra of 2.5 x 10$^{-4}$ M Poac$^7$-All in pH 3, 6 and 9.

US 6,797,829 B1

SYNTHESIS OF A NOVEL PARAMAGNETIC AMINO DERIVATIVE (EPM-5) FOR LABELLING CHEMICAL AND BIOLOGICAL MACROMOLECULES

FIELD OF THE INVENTION

This invention relates to the chemical synthesis of a new paramagnetic β-amino acid derivative containing a stable nitroxide radical moiety inserted in its pyrrolidine structure and in which the 9-fluorenylmethyloxycarbonyl group (Fmoc) was chosen as its amine function protecting group. This paramagnetic compound is a new type of spin probe (or spin label) and can be used as alternative report molecule for labeling peptide sequences, other macromolecules and systems where electron paramagnetic resonance spectroscopy (EPR) can be applied. This compound can be used also for other spectroscopic methods such as fluorescence and nuclear magnetic resonance since its paramagnetism may affect the spectra of these methodologies. Due to the presence of both carboxyl and amine groups in its structure, this organic compound may be used for labeling a great variety of other molecules or systems containing reactive functions for these two groups.

BACKGROUND AND SUMMARY OF THE INVENTION

The intermediate for the synthesis of the amino acid derivative of this invention contains the structure 2,2,5,5-tetramethylpyrrolidine-1-oxyl-3-amine-4-carboxylic acid, henceforth denominated as Poac, synthesized more than two decades ago (see, Tetrahedron 491–499 [1965] and Bull. France, 3, 815–817 [1967]). The Poac derivative containing the Fmoc protecting group (2,2,5,5-tetramethylpyrrolidine-1-oxyl-3-(9-fluorenylmethyloxycarbonyl)-amine-4-carboxylic acid is the novel spin probe derivative of the present invention, which also includes the synthesis and use in EPR of this spin probe derivative. This new compound allows the insertion of Poac as a usual amino acid at any position of a peptide sequence, and its denomination will be Fmoc-Poac or EPM-5 in this application. The chemical structure of this paramagnetic molecule is represented in FIG. 1.

Electron paramagnetic resonance (EPR) [described in *Biological Magnetic Resonance*, Berliner, L. J. and Reuben, J., eds., Plenum Publishing, New York, (1989)], is a modern and very usefull spectroscopic method because it allows the study of paramagnetically labeled macromolecules or biological systems regarding their conformation, mobilities, inter- or intra-molecular interactions, structuring states, and the like. The wide spectrum of EPR application is already detailed in the literature (see, *Free Nitroxyl Radical*, Rozantsev, E. G., Ulrich, H., ed., Plenun Press, London, 1970), where a great variety of spin labels, i.e., chemical compounds which are paramagnetic due to the presence of an unpaired electron in their structure, is listed. They are, therefore, a class of free radicals but are necessarily stable under conditions around normal temperature and physiological pH and also allow several chemical reactions or experiments without affecting their free radical moiety.

Amongst the most commonly used spin labels one can pick out the nitroxide group-containing molecules and where the unpaired electron locates. The most significant progress in the EPR field for labeling of relevant biological structures such as peptides and proteins was achieved with this class of spin probes. Almost two decades ago appeared the first EPR application in the solid phase peptide synthesis methodology [(*The Peptides: Analysis, Synthesis and Biology*, vol. 2, Academic Press, New York, (1980)]. This approach was introduced by our group using, instead, another nitroxide-containing spin label, denominated at that time as Toac (2,2,6,6tetramethylpiperidine-1-oxyl-4-amine-4-carboxylic acid), which protected its amine function with the acid labile tert-butyloxycarbonyl (Boc) group [(see, Braz. J. Med. Biol. Res. 14, 173, (1981) and Biochim. Biophys. Acta, 742, 63, (1983)]. Thus the Boc-Toac spin probe was the first in the literature used to label a peptide sequence as an amino acid. However, due to chemical particularities of the peptide synthesis methodology, it was only possible to couple the Toac group at the peptide N-terminal position. To overcome this shortcoming, an alternative strategy was published by us which finally allowed the insertion of the spin label internally to the peptide sequence [see, J. Am Chem. Soc. 115, 11042 (1993)].

An impressive increase in the application of EPR for peptide chemistry field was further observed in reports investigating peptide conformational properties [v.g J. Am. Chem. Soc. 117, 10555 (1995); FEBS Lett. 375, 239 (1995); Biopolymers 42, 821 (1997)]or of peptidyl-resin solvation (Tetrahedron Lett. 375, 239 [1995]; Biopolymers 42, 821 [1997]). As an amino acid, Toac was introduced in different positions of some biologically active peptides such as angiotensin II and bradykinin, but a partial or total loss of their biological potencies were observed due to the introduction of a non natural compound in their structures. [*Peptides 1996*, R. Ramage and R. Epton, eds., Mayflower Scientific Co. p.673 (1998)].

However, we recently described the synthesis of a peptide hormone labeled with Toac where its biological potency was entirely preserved. [e.g., FEBS Lett. 446, 45 (1999)]. This result was obtained with the tridecapeptide α-melanocyte stimulating hormone analogue, owing to its potentialities in a great number of chemical-biological assays (this analogue is paramagnetic, naturally fluorescent and fully active, and was disclosed in commonly owned U.S. patent application Ser. No. 09/935,760, entitled "Paramagnetic And Active Analogue (EPM-2) Of Melanocyte Stimulating Hormone Containing Amino Acid-Type Stable Free Radical").

In spite of these results, one still remaining shortcoming in the use of Toac in peptide chemistry is the severe difficulty in coupling the subsequent amino acid residue of the peptide sequence during the synthesis. This difficulty seems to be due to the low nucleophilicity of the Toac amine group, whose pKa of 8 (when in free state) decreases to about 5.5 when bound to the N-terminal portion of a peptide chain [v.g Braz J. Med. Biol. Res. 14, 173 (1981) and Biochim. Biophys. Acta. 742, 63 (1983)]. Several recouplings and an increase in the temperature of the coupling reaction are usually necessary to assure complete incorporation of the subsequent amino acid of the desired peptide sequence [J. Am. Chem. Soc. 115, 11042 (1993)].

DETAILED DESCRIPTION OF THE INVENTION

In order to overcome the limitations of the Toac probe to find an alternative spin label which may induce differentiated conformational constraints in peptide structures in accordance with this invention, we synthesized Fmoc-Poac according to the synthetic route shown below that is partially described in Tetrahedron, 491–499 (1965); Bull. Soc.Chim. France, 3, 815 (1967):

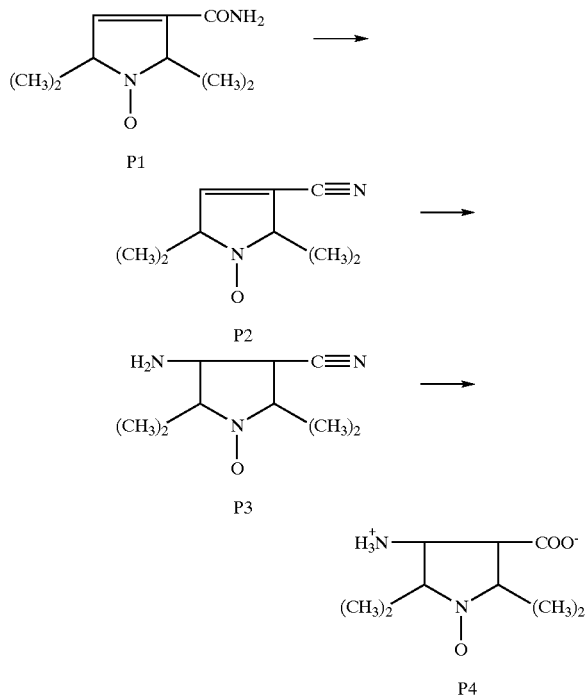

Step 1—Synthesis of 2,2,5,5-tetramethylpyrroline-1-oxyl-3-cyano (P2)

This product was synthesized by treating compound P1 (from Sigma Co) with tosyl (p-toluenesulfonate) chloride in dry pyridine. To 28.7 g ($1.5 \times 10^{-1}$ mol) of tosyl chloride, 15.3 g ($8.35 \times 10^{-2}$ mol) of P1 dissolved in 100 mL of dry pyridine was added and left at room temperature for 48 hours. After this period, 10 g of KOH dissolved in 250 mL of water were added, and the mixture was heated up to 80° C. After cooling, the product was extracted with sulfuric ether, washed with diluted HCl, diluted $NaHCO_3$ solution, water and dried over anhydrous $Na_2SO_4$. After evaporation of the solvent under reduced pressure 12.76 g (yield=92%) of an orange powder was obtained and further purified in an alumina column using benzene as an eluent. The product (P2) showed a single spot in thin layer chromatography with following characteristics: M.P.=62–63° C., M+=165; Elementary analysis found: C, 65.36%, H, 7.50% e N, 17.10%; calculated: C, 65.43%, H, 7.93% e N, 16.96%).

Step 2: Synthesis of 2,2,5,5-tetramethylpyrrolidine-1-oxyl-3-amine-4-cyano (P3)

In a 3 L round bottom flask, 600 mL of liquid ammonia, 9 g ($5.44 \times 10^{-2}$ mol) of P2 and 120 mL of water were added. The flask was tightly closed to maintain the mixture under pressure and left at room temperature. After 3 days, the ammonia was eliminated and the product extracted with chloroform. The crude product crystallized from ether-petroleum ether yielded 9.37 g (yield=94%) of a yellow powder with the following characteristics: M+=182; P.F. 84–85° C.; Elementary analysis found: C 58.98%; H, 8.37%; N, 22.21%; calculated ($C_9H_{16}ON_3$): C, 59.31%; H, 8.85%; N, 23.06%).

Step 3—Synthesis of 2,2,5,5-tetramethylpyrrolidine-1-oxyl-3-amino-4-carboxylic-acid (P4) (Poac).

Figure 1:
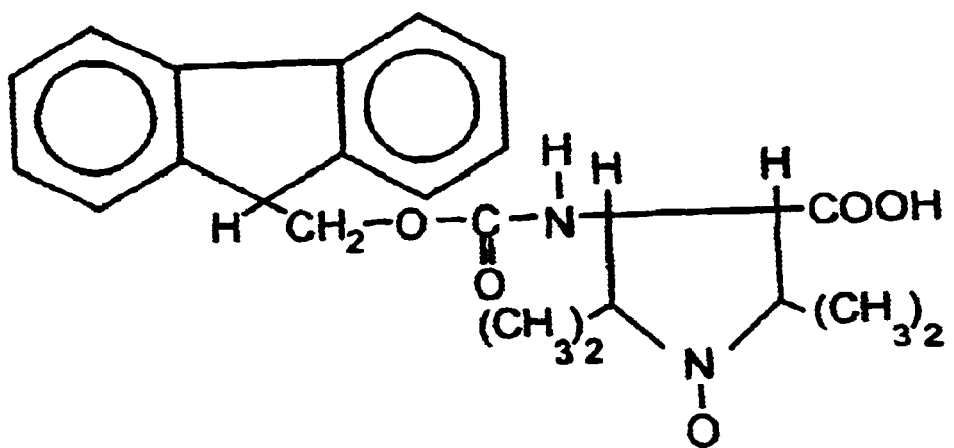
FIG. 1 is a depiction of the structure of Fmoc-Poac or EPM-5 according to this invention.
Figure 2:
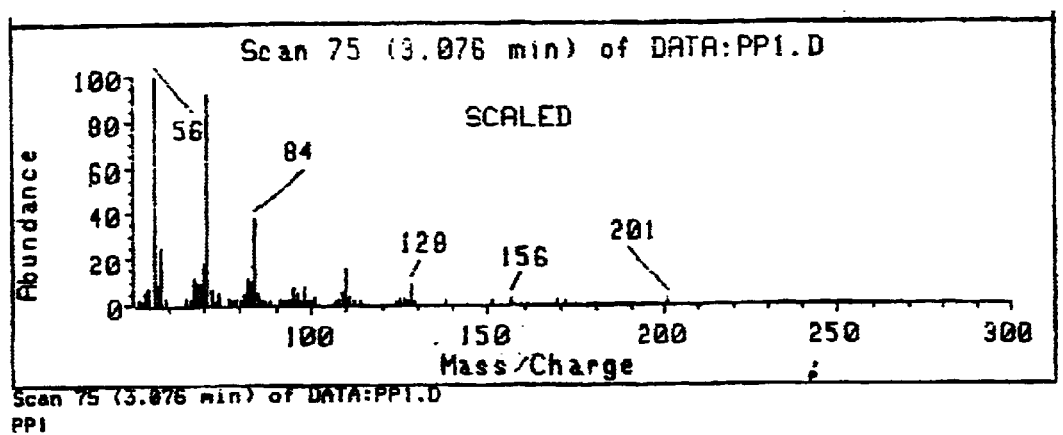
FIG. 2 is a mass spectrum of Poac.
Figure 3:
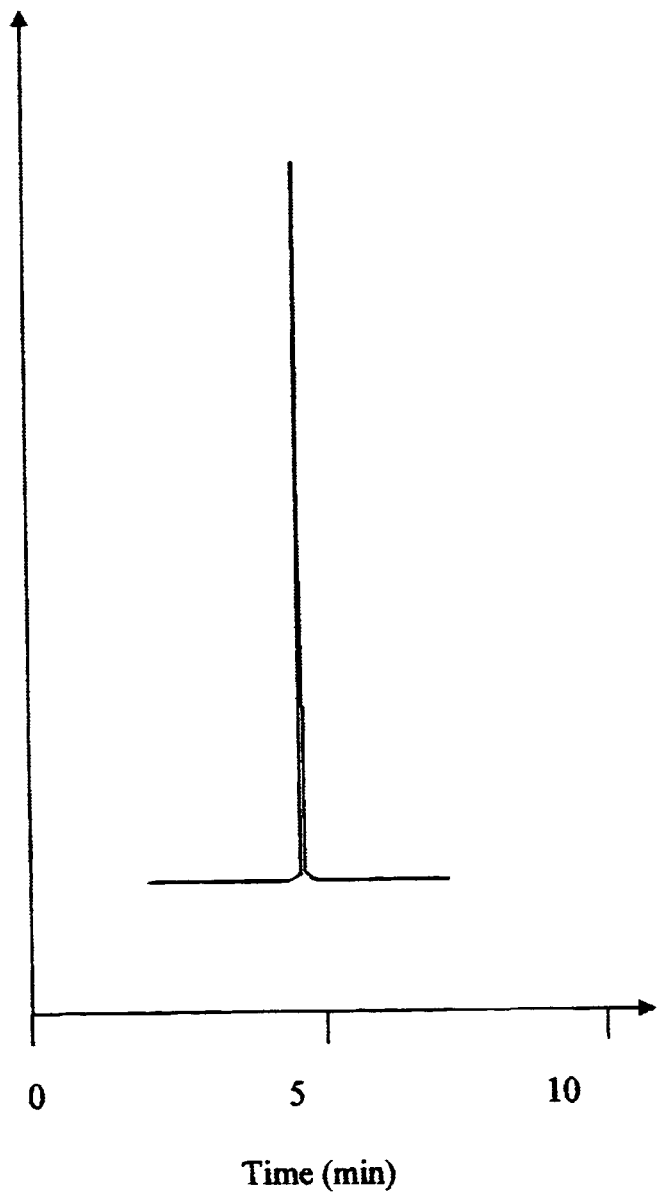
FIG. 3 is a high performance liquid chromatography (HPLC) profile of Poac showing a single peak.
Figure 4:
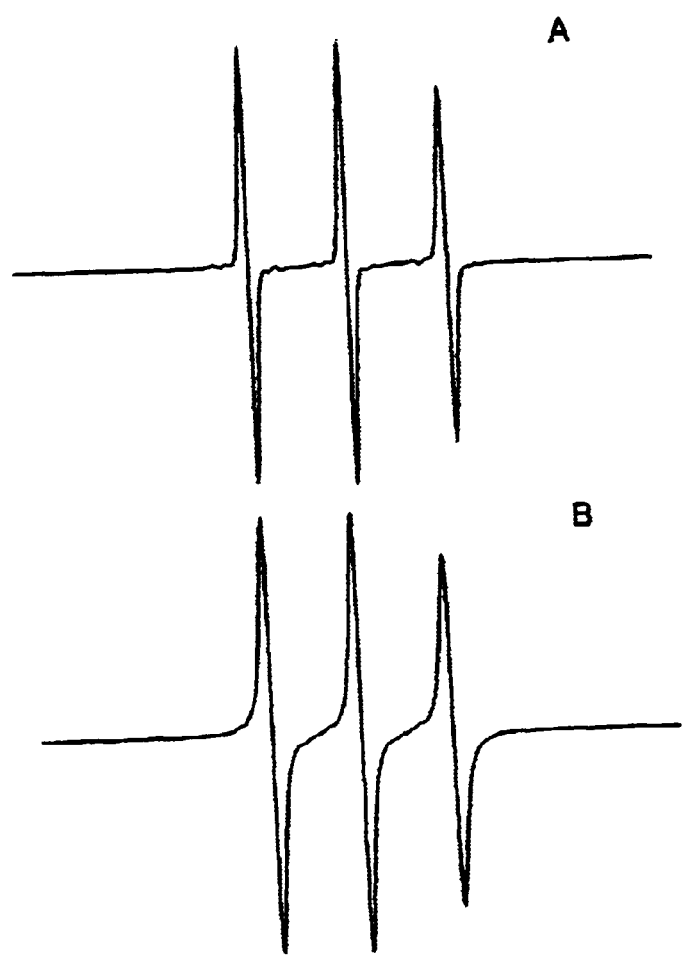
FIGS. 4A and 4B depict EPR spectra of Poac in water and Fmoc-Poac in dimethylformamide, respectively.

8 g ($4.38 \times 10^{-2}$ mol) of P3 and 40 g of $Ba(OH)_2$ were suspended in 600 mL of water and added to a 3 L round bottom flask. The flask was tightly closed and heated up to 120° C. for 90 minutes. After cooling, the mixture was neutralized with an excess of dry ice and filtered. The aqueous solution was concentrated under reduced pressure and yielded 8 g of crude product (yield: 90%) that was crystallized from 90% ethanol. The product presented the following characteristics: M.P.=212° C. (melts with sublimation); M+=201 (FIG. 2), single peak in HPLC (FIG. 3); elementary analysis found: C, 53.1%; H, 8.28%; N, 13.95%; calculated ($C_9H_{17}N_2O_3$): C, 53.71%; H, 8.52; N, 13.92 Infra-red (KBr): cm$^{-1}$: 3084, 2872, 2792, 2548 and 2132 (NH+3); 1643 $v_{AS}$ (NH+3); 1574 ($v_{AS}$, C=O); 1456 ($\delta CH3$); 1396 and 1376 (gem-dimethyl and COO—); 782 ($\delta C=O$). FIG. 4A shows the EPR spectrum of POAC in aqueous solution, pH 5. The calculated values for the two rotational correlation times ($\tau_B$ and $\tau_c$) were $0.509 \times 10^{-10}$ and $0.597 \times 10^{-10}$, respectively.

Figure 5:
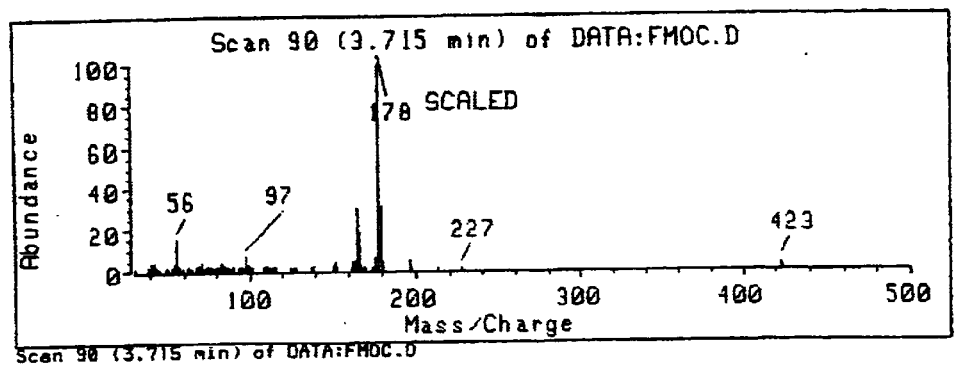
FIG. 5 is a mass spectrum of Fmoc-Poac.

Preparation of Fmoc-Poac 201 mg (1 mmol) of P4 was dissolved in 1.5 mL of water in presence of 286 mg of sodium carbonate $10H_2O$ in which 337 mg (1 mmol) of Fmoc-succinimidyl-carbonate dissolved in 1.5 mL of acetone was added drop-wise. The reaction was carried out at room temperature with stirring, and the pH was maintained around 9 by addition of sodium carbonate. After 3 hours, the mixture was diluted with 25 mL of water and acidified with 1 N HCl until it reached pH 2. The desired product was extracted with ethyl acetate, washed with small portions of water, dried over anhydrous sodium sulfate. After filtration, the solvent was evaporated under reduced pressure. The crude product was crystallized twice with chloroform and yielded 380 mg (yield: 90%). The product was characterized by mass and infra-red spectroscopy, elementary analysis and EPR. Characteristics: M+=423 (FIG. 5); elementary analysis found: C, 67.9%; H, 6.35%; N, 6.60; calculated ($C_{24}H_{27}O_5N_2$): C, 68.08%; H, 6.28%; N, 6.62%; IR (KBr) cm$^{-1}$: 3444–3338 (broad band OH and —CONHR); ~3030 (vAr CH); 3000–2700 (vAr COOH); 1723 (R—O—C—ON— and COOH); 1543 ($\delta_{NH}$ and vCN); 1450 ($\delta CH_3$); 1235–1150 (gem-dimethyl group). The EPR spectra of Fmoc-Poac in dimethylformamide is represented in FIG. 4B and the calculated $\tau_B$ and $\tau_c$ values are $1.14 \times 10^{-10}$ s.rad$^{-1}$ and $1.79 \times 10^{-10}$ s.rad$^{-1}$, respectively.

Synthesis of Poac[7]-angiotensin II

Angiotensin II analogue labeled with the spin probe Poac (Asp-Arg-Val-Tyr-Ile-His-Poac-Phe) was synthesized in 0.15 mmol scale, by the solid phase method already mentioned and with alteration to provide the insertion of this maker in the middle of the peptide chain. [J. Am. Chem. Soc. 115, 11042 (1993)]. Fmoc-Phe-Wang-resin [J. Am. Chem. Soc. 95, 1328 (1973)] with 0.41 mmol/g substitution degree acquired commercially was used. All couplings were carried out using 2.5 fold excess for the Fmoc-amino acids and 3 fold excess for Fmoc-Poac. The acylating reagents for coupling were diisopropylcarbodiimide (DIC) and 1-hydroxybenzotriazole in a dichloromethane:dimethylformamide mixture (1:1, v/v) as a solvent. The Fmoc deprotection was performed with 20% piperidine in dimethylformamide (v/v) for 20 min.

Interestingly, this synthesis demonstrated that the pyrrolidine structure of the Poac spin label allowed much easier incorporation of the subsequent amino acid residue than has been observed during the Toac[7]-AII synthesis. In this latter case, repetitive recoupling reactions were necessary, including an increase in temperature. These procedures were not necessary in the case of the Poac derivatives, thus demonstrating that the Poac amine group reactivity is much higher than that of Toac.

After the completion of the synthesis, the peptide was cleaved from the resin in anhydrous HF containing 10% of a p-cresol and dimethylsulfide mixture, at 0° C. for 90 min. The crude peptide obtained after extraction and lyophilization (125 mg) was dissolved in 70 mL of water and the pH was raised to 10 with ammonium hydroxide and stirred for 2 h, to reverse the nitroxide protonation that occurs during the HF treatment. After lyophilization, the peptide was purified by preparative HPLC (high performance liquid chromatography) using a reverse phase $C_{18}$ (25×250 mm) and ammonium acetate 0.02 M, pH 5 and acetonitrile 60% in water, as solvents A and B, respectively. The linear gradient applied was from 20–65% of B for 135 min.

Figure 6:
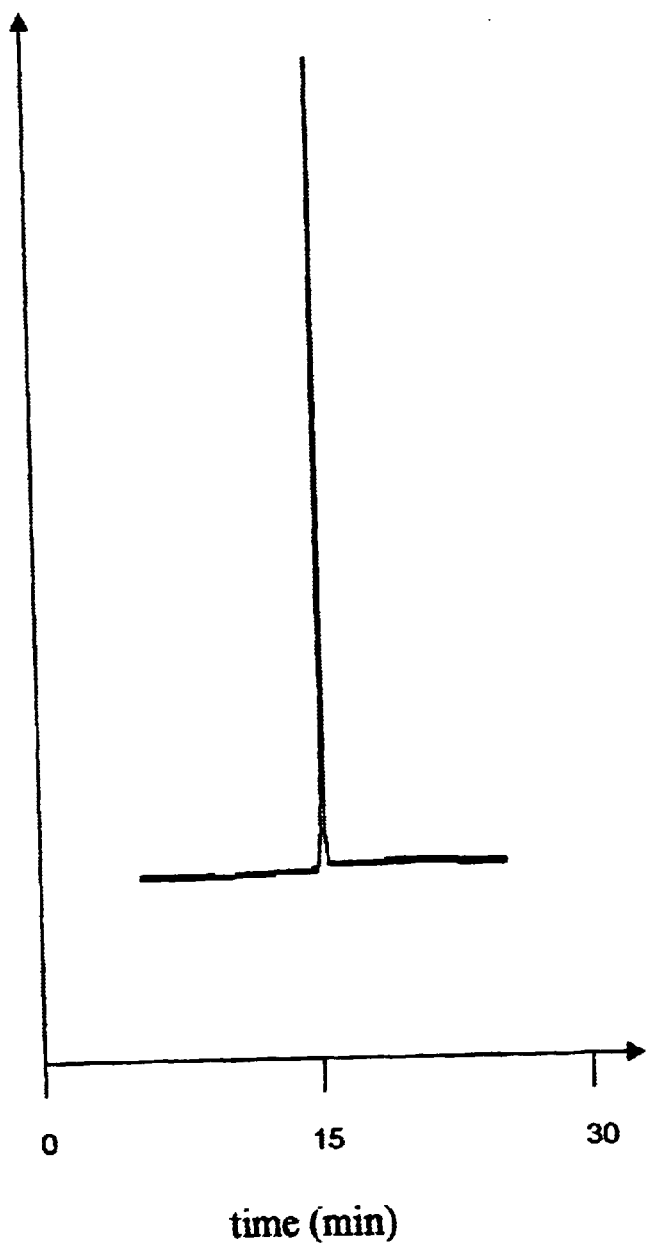
FIG. 6 is a HPLC profile of Poac[7] showing a single peak.
Figure 7:
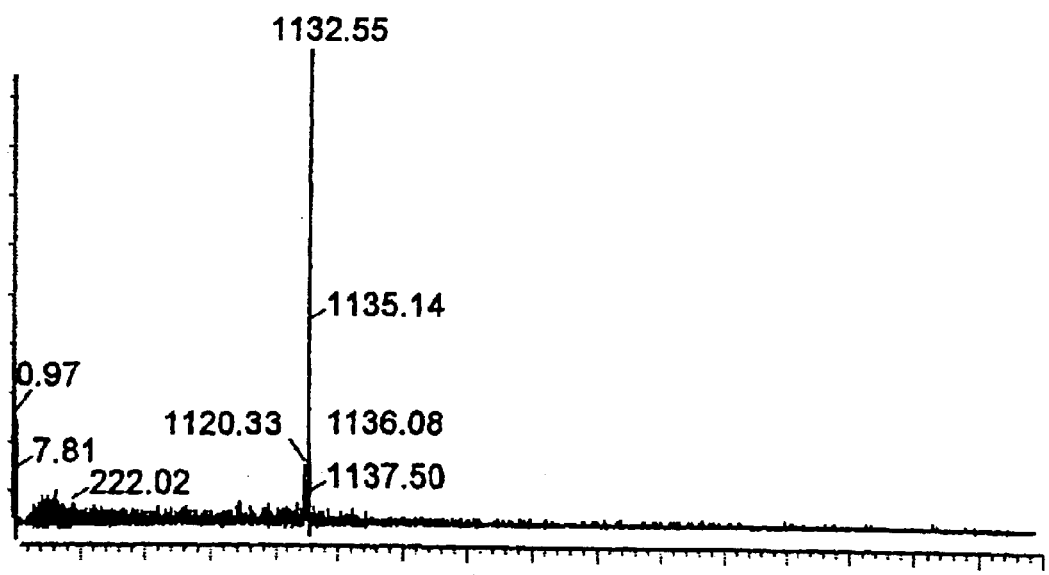
FIG. 7 is a mass spectrum of Poac[7]-angiotensin II.
Figure 8:
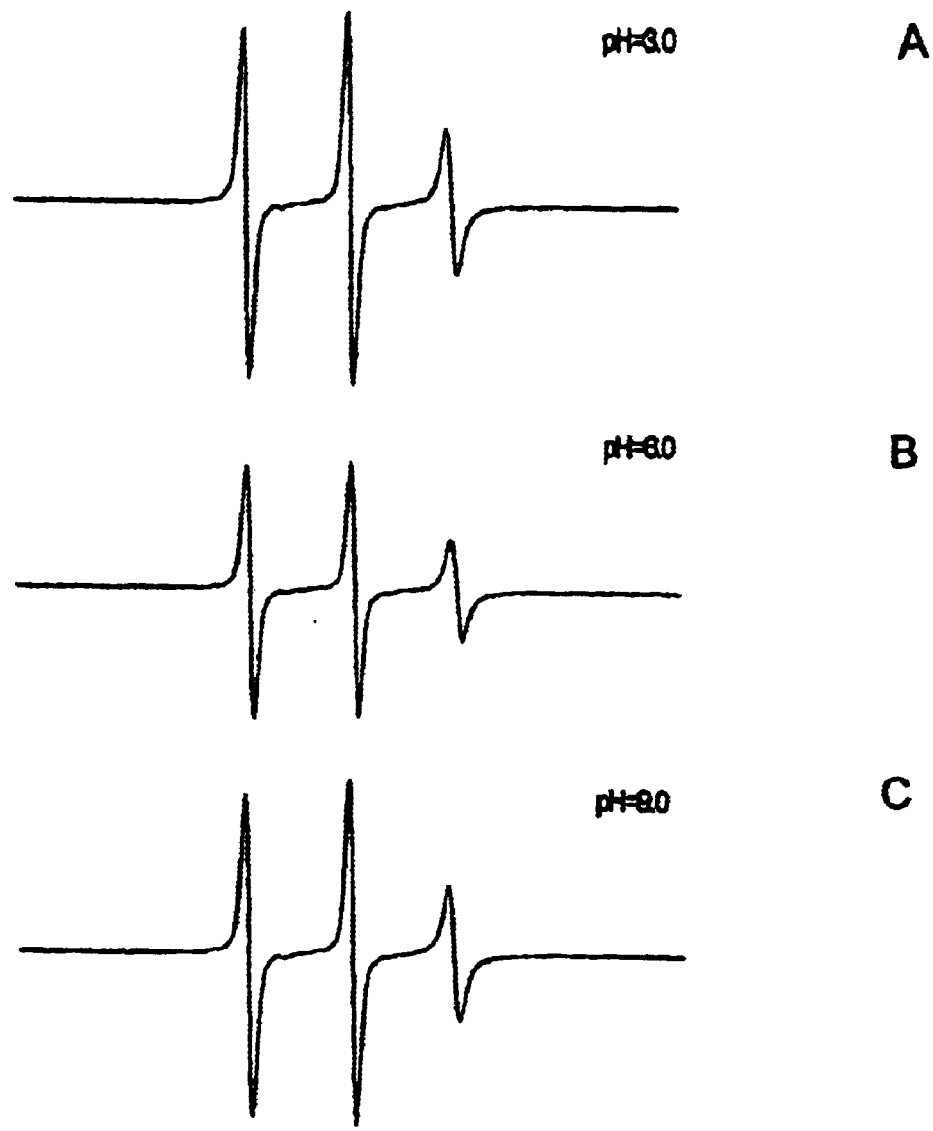
FIGS. 8A, 8B and 8C depict EPR spectra of Poac[7]-angiotensin II at pH 3.0, 6.0 and 9.0, respectively.

The homogeneity of the peptide was confirmed through analytical HPLC (FIG. 6), mass spectrometry, M+=1132.55 (FIG. 7), and the amino acids analysis showed the expected composition: Asp 0.95 (1.00); Val 0.96 (1.00); Ile 1.20 (1.00); Tyr 1.02 (1.00); Phe 1.00 (1.00); His 0.96 (1.00); Arg 1.02 (1.00). FIG. 8 displays the EPR spectra of 0.25 mM Poac[7]-AII at pH 3, 6 and 9 aqueous solution No significant variation on the rotational correlation time values was observed for this paramagnetic AII analogue thus suggesting that its conformation is not affected by the pH of the media.

What is claimed is:

1. 2,2,5,5-tetramethylpyrrolidine-n-oxyl-(9-fluorenylmethyloxycarbonyl)-3-amine-4-carboxylic acid.

2. Poac[7]-Angiotensin II (Asp-Arg-Val-Tyr-Ile-His-Poac-Phe).

3. A method of labeling a molecule or system for chemical or biochemical study, comprising coupling the molecule or system with 2,2,5,5-tetramethylpyrrolidine-n-oxyl-(9-fluorenylmethyloxycarbonyl-3-amine-4-carboxylic acid.

4. The method of claim 3, wherein the chemical or biochemical study is electron paramagnetic resonance.

5. The method of claim 3, further comprising removing the 9-fluorenylmethyloxycarbonyl group from the 2,2,5,5-tetramethylpyrrolidine-n-oxyl-(9-fluorenylmethyloxycarbonyl)-3-amine-4-carboxylic acid to produce the molecule or system with an unprotected Poac derivative.

6. The method of claim 5, further comprising coupling a chemical group at a free amine function of the molecule or system containing the unprotected Poac derivative.

7. The method of claim 3, wherein the molecule is angiotensin-II.

* * * * *

UNITED STATES PATENT AND TRADEMARK OFFICE
CERTIFICATE OF CORRECTION

PATENT NO. : 6,797,829 B1
DATED : September 28, 2004
INVENTOR(S) : Clovis R. Nakaie et al.

It is certified that error appears in the above-identified patent and that said Letters Patent is hereby corrected as shown below:

Title page,
Item [75], Inventors, please change "Antonio Cechlli Matto Paiva," to -- Antonio Cechelli de Mattos Paiva -- and "Reinaldo Machetto" to -- Reinaldo Marchetto --

Signed and Sealed this

Twelfth Day of April, 2005

JON W. DUDAS
*Director of the United States Patent and Trademark Office*